US00PP17836P3

(12) United States Plant Patent
Petersen

(10) Patent No.: US PP17,836 P3
(45) Date of Patent: Jun. 26, 2007

(54) PISTACHIO PLANT CALLED 'PETE I'

(50) Latin Name: ***Pistacia* sp.**
Varietal Denomination: PETE I

(75) Inventor: David R. Petersen, Chico, CA (US)

(73) Assignee: Pete I Pistachios, Inc., Chico, CA (US)

( * ) Notice: Subject to any disclaimer, the term of this patent is extended or adjusted under 35 U.S.C. 154(b) by 298 days.

(21) Appl. No.: 10/966,796

(22) Filed: Oct. 14, 2004

(65) Prior Publication Data

US 2006/0085876 P1 Apr. 20, 2006

(51) Int. Cl.
*A01H 5/00* (2006.01)

(52) U.S. Cl. ..... Plt./152

(58) Field of Classification Search ..... Plt./152
See application file for complete search history.

*Primary Examiner*—Kent Bell
*Assistant Examiner*—June Hwu
(74) *Attorney, Agent, or Firm*—Christie, Parker & Hale, LLP

(57) ABSTRACT

A new and distinct pistachio tree named 'PETE I', characterized by a very white shell nut with a 90% or higher split ratio and a large nut size (18 to 20 nuts per ounce), nut meat color brilliant purple on the exterior with a dark green interior, a very high resistance to *Botryosphaeria panicle* and shoot blight (*Botryosphaeria dothidea*) fungus, large, dark green leaves and an early bloom.

5 Drawing Sheets

Botanical classification: *Pistacia* sp.
Cultivar name: 'PETE I'.

BACKGROUND OF THE INVENTION

The present invention relates to a new and distinct variety of pistachio tree, propagated from a T-budding sport.

Naturally occurring sports were collected, budded onto existing Pioneer Gold II rootstock, and analyzed for resistance to the fungus *Botryosphaeria panicle* and shoot blight (*Botryosphaeria dothidea*). One sport was selected for its high resistance to the fungus and designated 'PETE I'. The parents of 'PETE I' are unknown.

SUMMARY OF THE INVENTION

The 'PETE I' variety is characterized by a very white shell nut with a 90% or higher split ratio and a large nut size (18 to 20 nuts per ounce). Nut meat color is brilliant purple on the exterior with a dark green interior.

'PETE I' is further characterized by a very high resistance to *Botryosphaeria panicle* and *Botryosphaeria dothidea,* a major pistachio fungus, when compared to 'Kerman', 'Kalleh Ghoochi', and other pistachio varieties.

'PETE I' has a very upright growth habit. In the pre-harvest years (1 to 6 years), vegetative growth exceeds four feet per year with flower buds appearing in the fourth year. Leaves are deep green in color, compound with three to five, average of three, leaflets. During years 1 to 3, leaflets are noticeably larger, sometimes exceeding six inches in length and width. 'PETE I' trees have very dense foliage during the early years, becoming more aerated with maturity.

'PETE I' pollinates early compared to 'Kerman', typically 5 to 7 days earlier. First flowers are receptive in late March compared to early April for 'Kerman'. Flowers are consistent in size and conformation, with an inverted Christmas tree appearance. Early pollination gives 'PETE I' a competitive advantage over varieties like 'Kerman' in that nuts of 'PETE I' will be ready for market earlier than those of 'Kerman' and other varieties.

Asexual reproduction by budding onto a Pioneer Gold II rootstock at Butte County, Calif. shows that the foregoing and other distinguishing characteristics come true to form and are established and transmitted through succeeding propagation. Other known forms of asexual reproduction for pistachios may also be employed.

BRIEF DESCRIPTION OF ILLUSTRATIONS

The accompanying photographic illustrations show typical specimens of vegetative growth of the new variety, in color as nearly true as it is reasonably possible to make in a color illustration of this character.

COMPARISON TO 'KERMAN'

The closest commercial equivalent to 'PETE I' of which I am aware is 'Kerman'. The new variety differs from 'Kerman' in the following characteristics:

TABLE 1

Comparison of 'Pete I' to 'Kerman'

| | 'PETE I' | 'Kerman' |
|---|---|---|
| Nuts | White shell with brilliant green meat. Clusters are spectacular in density (20 to 30 nuts/cluster). Open - splits 90% or more with a high percentage of 20 to 30 nuts/cluster. | White shell with a pale green meat. Clusters are less dense (10 to 15 nuts/cluster). Open - splits 75–80% with a higher degree of non-splits. |
| Disease Resistance | High degree of resistance to *Botryosphaeria panicle* and *Botryosphaeria dothidea*. In mature trees, average occurrence of *botryosphaeria* in 'PETE I' is about 5 strikes/tree, compared to 100 strikes/tree for 'Kerman'. | Very low resistance to *Botryosphaeria panicle* and *Botryosphaeria dothidea*, especially in areas of heavy rainfall. Average occurrence of *Botryosphaeria panicle* and *Botryosphaeria dothidea* in 'Kerman' is about 100 strikes/tree, compared to 5 strikes/tree for 'PETE I'. |
| Growth Habits | Upright growth with large, dark green leaves; typically 3 leaflets. Grows 3–4 feet/year with flower buds appearing in the 4th year. | Upright growth with average size leaves; usually 5 leaflets. Grows 3–4 feet/year with flower buds appearing in the fifth year. |
| Pollination | Blooms in late March through early April (typically, March 25 through April 10, in Butte county, California). | Blooms in early April (typically March 30 through April 15, in Butte county, California). |

DESCRIPTION OF THE NEW VARIETY

Referring now specifically to the new and distinct variety of pistachio tree, the following is a detailed description of 18 year old plants with color description where indicated by reference to The Royal Horticultural Society Colour Chart, except where common terms of color definition are employed.

The new variety of pistachio tree as herein described may vary in slight detail due to climatic, soil and cultural conditions under which the variety may be grown, the present description being of the variety as grown at Butte County, Calif.

Figure 1:
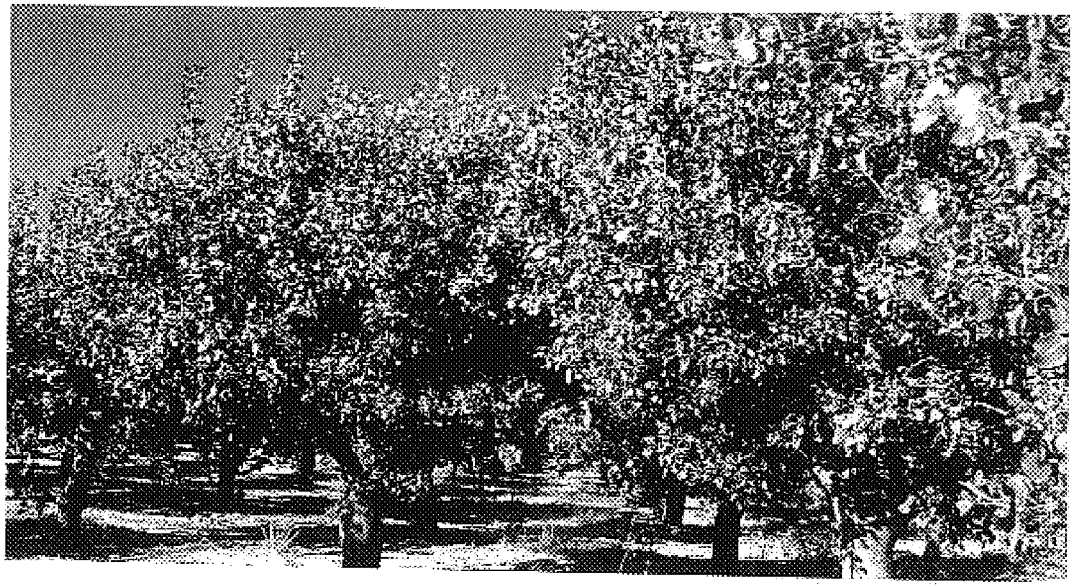
FIG. 1 shows an 18 year old pistachio tree of the new variety.

Plant:

*Shape.*—Symmetric canopy as shown in FIG. 1, about 16 feet in diameter.

*Height.*—About 17 to 18 feet at maturity.

*Growing habit.*—Before maturity, growth is cane in appearance, growing approximately 3 to 4 feet per year. At maturity, growth is 1 to 2 feet per year.

*Branching habit.*—Established trunk with primary scaffolds starting in about the 40-inch range. Growth is cane-like in vegetation with smaller fruiting spears.

*Disease resistance.*—High resistance to *Botryosphaeria panicle* and *Botryosphaeria dothidea* fungus.

Trunk:

*Dimensions.*—At union (about 2 feet), diameter 15 inches and circumference 45 inches.

*Surface texture.*—Rough.

*Coloration.*—Grey-Brown (near 199B) to Grey-Green (near 198B).

Branching:

*Dimensions.*—Approximately 6 to 8 in number; about 4 feet in length, 6 to 7 inches in diameter at maturity.

*Surface texture.*—Smooth.

*Lenticel coloration.*—White, near 155 B.

Figure 2:
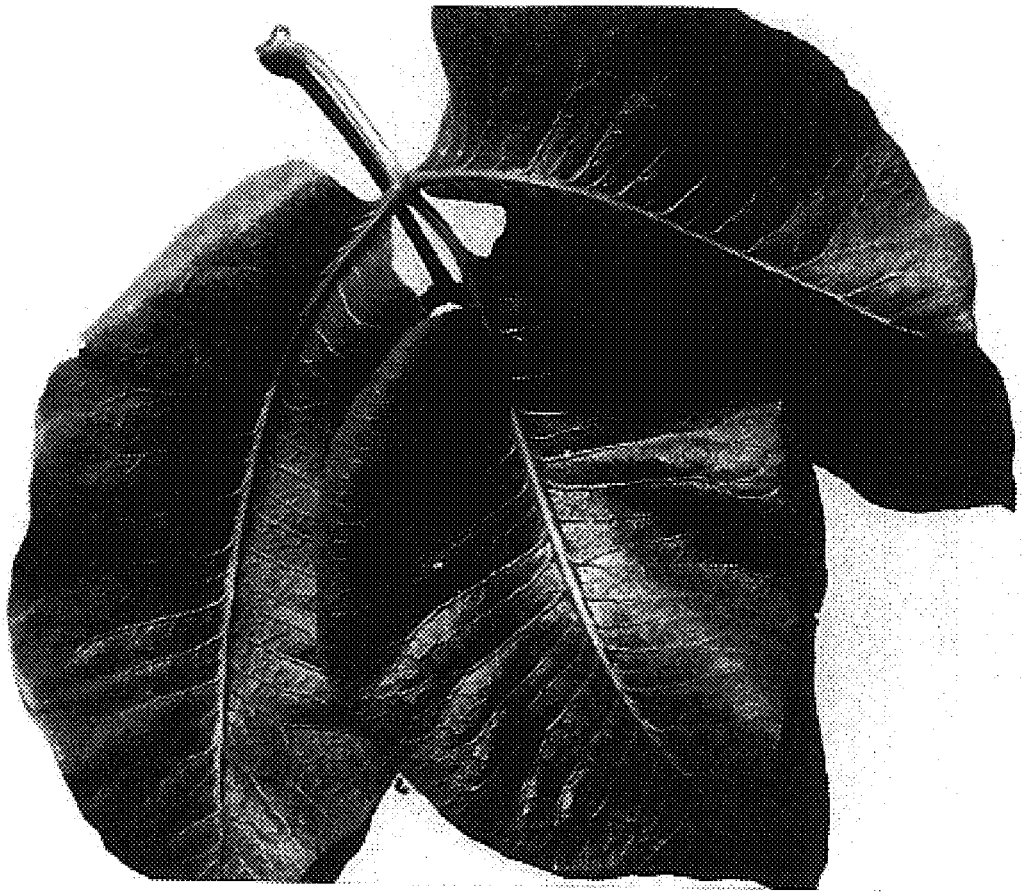
FIG. 2 shows a close-up of a leaf of the new variety.
Figure 3:
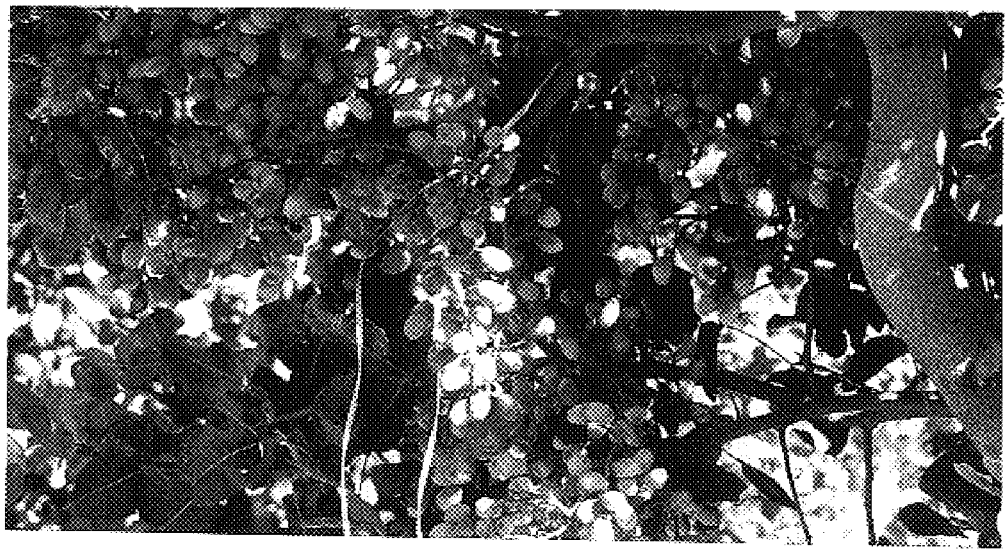
FIG. 3 shows a close-up of clusters of nuts of the new variety.
Figure 4:
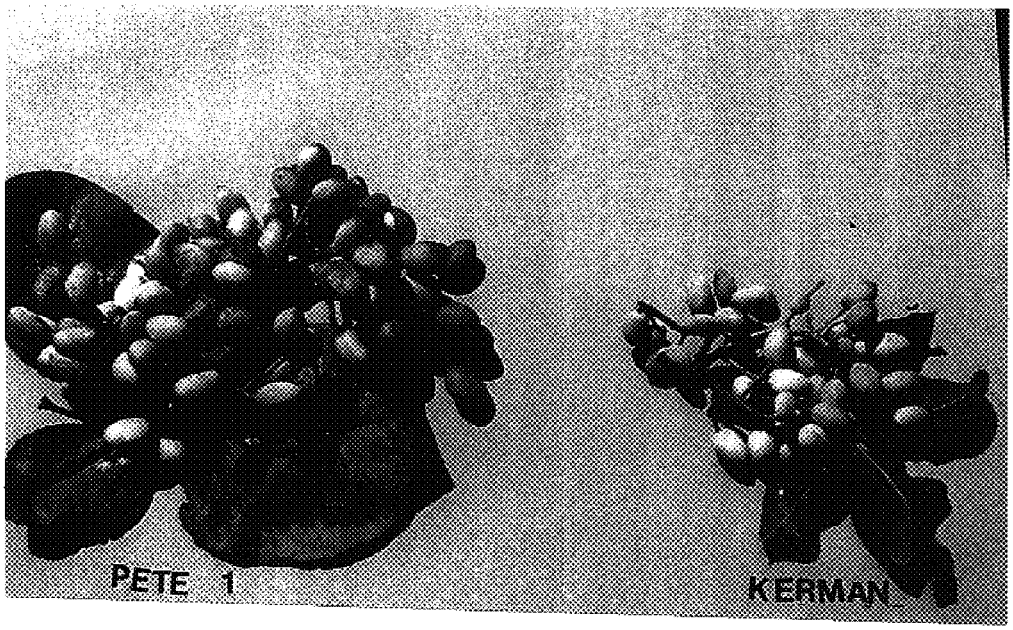
FIG. 4 shows a close-up comparison of the leaves and nut clusters of the new variety and 'Kerman'.
Figure 5:
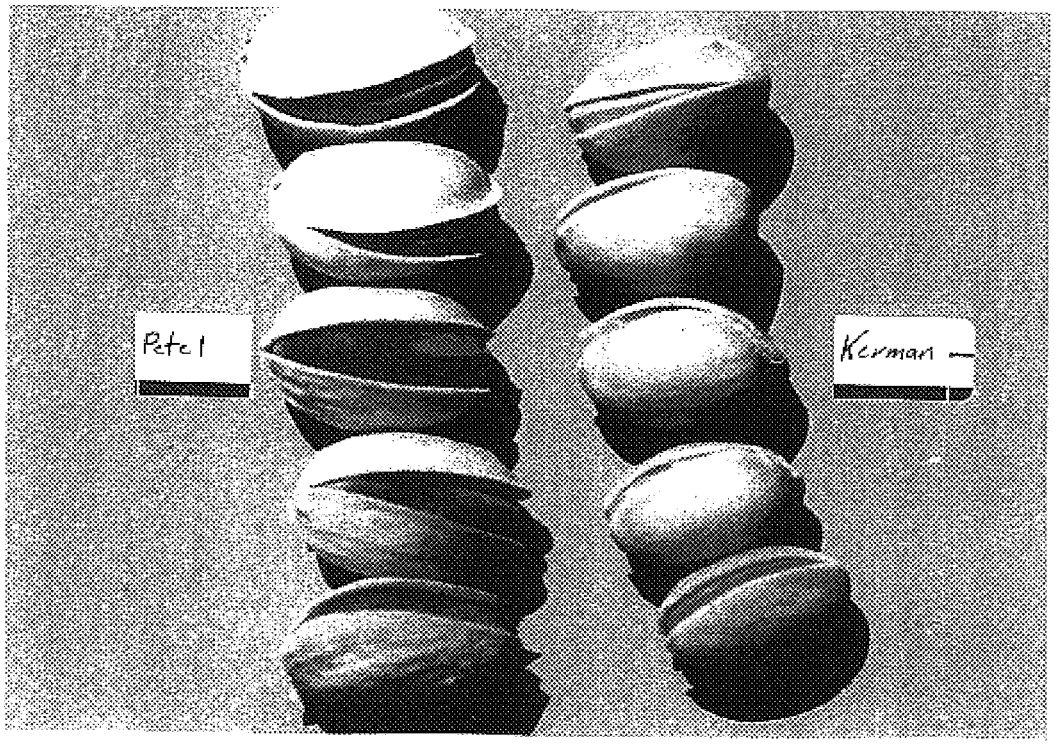
FIG. 5 shows a close-up comparison of nuts of the new variety and 'Kerman'.

Foliage:

*Leaf arrangement.*—Compound, three to five leaflets, with an average of three, as shown in FIG. 2.

*Color.*—Upper and lower surfaces: green, near 138A.

*Surface texture.*—Upper and lower surfaces: glabrous.

*Compound leaf dimension.*—Length: at maximum about 6 to 8 inches; width: at maximum about 7 to 9 inches.

*Leaflet size/shape.*—Length: about 4 to 6 inches; width: about 4 to 6 inches; shape oval.

*Leaflet base.*—Broadly cuneate.

*Leaflet apex.*—Obtuse.

*Leaflet margin.*—Entire to slightly repand.

*Petiole length.*—About 4 to 6 inches.

*Petiole color.*—Light yellow-green, near 147C-147D.

Bloom:

*Form.*—Inverted Christmas tree appearance.

*Borne.*—Typically 3 to 7 flowers per lateral stem.

*Flowering season.*—Late March through mid-April.

*Flower diameter.*—Base: about 2 to 3 inches; tip: about ½-inch.

*Flower depth.*—About 6 inches at the end of bloom.

*Flower coloration.*—Red, near 47A.

Reproductive organs:

*Pistil.*—Yellow-Green, near 151C-151D.

*Nuts.*—Husk thickness — About 1/16 inches. Shell color — Very white, near 155C-155D. Size — About ¾ inches wide and about 1.5 inch long on average. Shape — Oval. Surface texture — Smooth. Number per inflorescence — About 15 to 25. Number per ounce — About 18 to 20. Pellicle — Red-Purple, continuously varying across Group 66A-66D. Kernel size — About ½ inches wide and about 1 inch long on average. Kernel shape — Oval. Kernel texture — Irregular. Kernel color — Exterior: brilliant purple, near 61B; interior: dark green, near 144A-144B. Split ratio — 90% or higher. Kernel flavor — Subtle, crisp nutty flavor.

Industrial usage: Nut is hulled, dried, sorted, roasted and salted, and packaged.

Keeping & shipping quality: Excellent in absence of excessive moisture.

Harvest information: Between August and September when grown in the California region.

We claim:

1. A new and distinct variety of pistachio tree, identified as 'PETE I', substantially as shown and described.

* * * * *